(12) United States Patent
Deshays

(10) Patent No.: US 7,982,199 B2
(45) Date of Patent: Jul. 19, 2011

(54) MEDICAL IMAGING APPARATUS

(75) Inventor: Clement Deshays, Ruoms (FR)

(73) Assignee: Germitec, Paris (FR)

( * ) Notice: Subject to any disclaimer, the term of this patent is extended or adjusted under 35 U.S.C. 154(b) by 367 days.

(21) Appl. No.: 12/091,232

(22) PCT Filed: Dec. 5, 2005

(86) PCT No.: PCT/FR2005/003034
§ 371 (c)(1),
(2), (4) Date: Apr. 23, 2008

(87) PCT Pub. No.: WO2007/048887
PCT Pub. Date: May 3, 2007

(65) Prior Publication Data
US 2008/0283769 A1 Nov. 20, 2008

(30) Foreign Application Priority Data

Oct. 26, 2005 (FR) ...................... 05 10958

(51) Int. Cl.
*A61N 7/00* (2006.01)
(52) U.S. Cl. ........................ 250/504 R; 250/372; 422/24
(58) Field of Classification Search ............. 250/504 R, 250/372; 422/24; 600/1
See application file for complete search history.

(56) References Cited

U.S. PATENT DOCUMENTS

| | | | |
|---|---|---|---|
| 4,772,795 A | 9/1988 | Sakurai et al. | |
| 5,185,532 A | 2/1993 | Zabsky et al. | |
| 5,690,113 A | 11/1997 | Sliwa, Jr. et al. | |
| 6,039,928 A | 3/2000 | Roberts et al. | |
| 6,171,559 B1 | 1/2001 | Sanders et al. | |
| 6,231,819 B1 | 5/2001 | Morello | |
| 2002/0162972 A1 | 11/2002 | Pleet | |
| 2004/0140347 A1 * | 7/2004 | Mihaylov et al. | ............... 232/31 |

FOREIGN PATENT DOCUMENTS

| | | |
|---|---|---|
| DE | 3209701 A | 9/1983 |
| EP | 0630820 A1 | 12/1994 |
| EP | 1 532 989 A1 | 5/2005 |
| WO | 84/00009 A | 1/1984 |
| WO | 99/08137 A | 2/1999 |

OTHER PUBLICATIONS

International Search Report of PCT/FR2005/003034, date of mailing Jul. 18, 2006.

* cited by examiner

*Primary Examiner* — Phillip A Johnston
*Assistant Examiner* — Hanway Chang
(74) *Attorney, Agent, or Firm* — Westerman, Hattori, Daniels & Adrian, LLP

(57) ABSTRACT

The invention concerns a medical imaging apparatus comprising a frame (2) whereon is mounted at least one medical imaging data processing unit (4) connected at least to imaging sensor forming means (5,7,8,9), and to image display forming means (6). The invention is characterized in that the frame (2) comprises at least one integrated chamber (11) for disinfecting the sensor forming means, including means for generating a disinfecting radiation and adapted to implement a sanitizing cycle thereof.

25 Claims, 4 Drawing Sheets

MEDICAL IMAGING APPARATUS

The present invention concerns a medical imaging apparatus.

More particularly, the invention relates to such an apparatus which includes a frame on which is mounted at least one medical imaging data processing unit connected at least to imaging sensor forming means and to image display forming means.

Such a medical imaging apparatus can be constituted, for example, by a sonogram apparatus, an endoscope, or other.

That is, a high number of medical imaging apparatuses have been provided in the state of the art.

However, these apparatuses have a number of drawbacks, in particular with respect to sensor disinfection.

Namely, the disinfection of such sensors is performed most of the time simply by wiping them, for example, with a cloth soaked with a disinfection substance of any type.

Other disinfection techniques require dipping the sensor in an appropriate disinfecting solution.

The problem of these disinfection techniques is that, either they are easy to implement, such as, for example, by wiping, but they do not make it possible in this case to obtain an optimal disinfection of the sensor, or they are more complex to implement, such as, for example, immerging the sensor in a disinfecting solution, but in that case, they are implemented in a more or less systematic manner.

Indeed, this last technique requires disconnecting the sensor from the sonogram apparatus, immerging it and letting it soak in the disinfecting solution, then reconnecting it to the sonogram apparatus.

However, such manipulations of the sensor can result in deteriorating it.

Namely, disconnecting and reconnecting the sensor can lead to deteriorating the corresponding connectors. Similarly, the sensor can also be damaged during its disinfection in the solution.

However, such sensors are quite expensive.

Further, these various disinfection techniques require that corresponding disinfection means be available, which disinfection means can on occasion be difficult to use or even require a specific containment.

The objective of the invention is to remedy these problems.

To this effect, an object of the invention is a medical imaging apparatus, of the type comprising a frame on which is mounted at least one medical imaging data processing unit, connected at least to imaging sensor forming means and to image display forming means, characterized in that the frame includes at least one integrated chamber for disinfecting the sensor forming means, including means for generating a disinfecting radiation and adapted to implement a disinfecting cycle thereof.

According to other characteristics of the invention:
the chamber is equipped with an access hatch and is associated with a control panel provided on the frame;
each sensor has identification data and the chamber is associated with means for acquiring the identification data of the or each sensor when it is put in place and when it is removed from the chamber at the start and at the end of a disinfecting cycle, with means for acquiring characterization data of the disinfecting cycle, and with means for associating the identification data of the or each instrument and the characterization data of the disinfecting cycle to generate traceability data of the disinfection of the or each sensor;
the identification data of each sensor is in the form of a bar code and the corresponding acquisition means of the chamber comprise a code reader;
the chamber includes a boom for suspending the sensor and the reader is fixed to this boom;
the means for acquiring characterization data of the disinfecting cycle comprise means for acquiring data selected from the data group comprising identification data of the chamber and/or of the apparatus and time-stamping data of the disinfecting cycle;
the chamber includes means for generating a UV radiation for disinfecting the sensor and the characterization data of the disinfecting cycle comprise data on the UV dose emitted during the cycle, provided by a corresponding sensing element implanted in the chamber.
the UV sensing element is implanted under the boom of the chamber;
the means for associating the data are associated with means for displaying this data, for storing this data, and/or for printing this data;
the means for associating this data are adapted to emit traceability data only if the corresponding sensor has actually been identified when it is put in place and when it is removed from the chamber before and after the disinfecting cycle, respectively;
the chamber has an interior surface having a circular cross-section;
the inner surface of the chamber has semi-circular recesses for receiving radiation generating means;
the radiation generating means include four tubes disposed at 90° with respect to one another;
the chamber has an inner surface covered at least in part by polytetrafluoroethylene;
the chamber has means for suspending at least one sensor in the chamber and means for rotating the sensor in the chamber;
the rotating means are adapted to trigger an oscillating movement over a predetermined angular range of the suspension means;
the rotating means comprise electric drive means associated with a hook for suspending the sensor in the chamber;
the suspension means and the drive means are associated with the boom extending in the chamber;
the chamber has means for suspending at least one sensor in the chamber and means for generating in the chamber a disinfection radiation, and means transparent to the radiation for holding the sensor in an elongated state and in a substantially vertical orientation under the suspension means;
the holding means are adapted to hold the sensor substantially at the center of the chamber;
the holding means comprise means for guiding the sensor in the chamber;
the guiding means include one or several members in the form of combs for guiding the sensor distributed over the height of the chamber;
the guiding means comprise one or several tubes for receiving the sensor;
the holding means comprise a weight adapted to be coupled at the free end of the sensor; and
the holding means are made in silicium oxide.

The invention will be better understood by reading the following description given by way of example only, in reference to the annexed drawings, in which:

FIGS. 1 and 2 illustrate an embodiment of a medical imaging apparatus.

Figure 1:
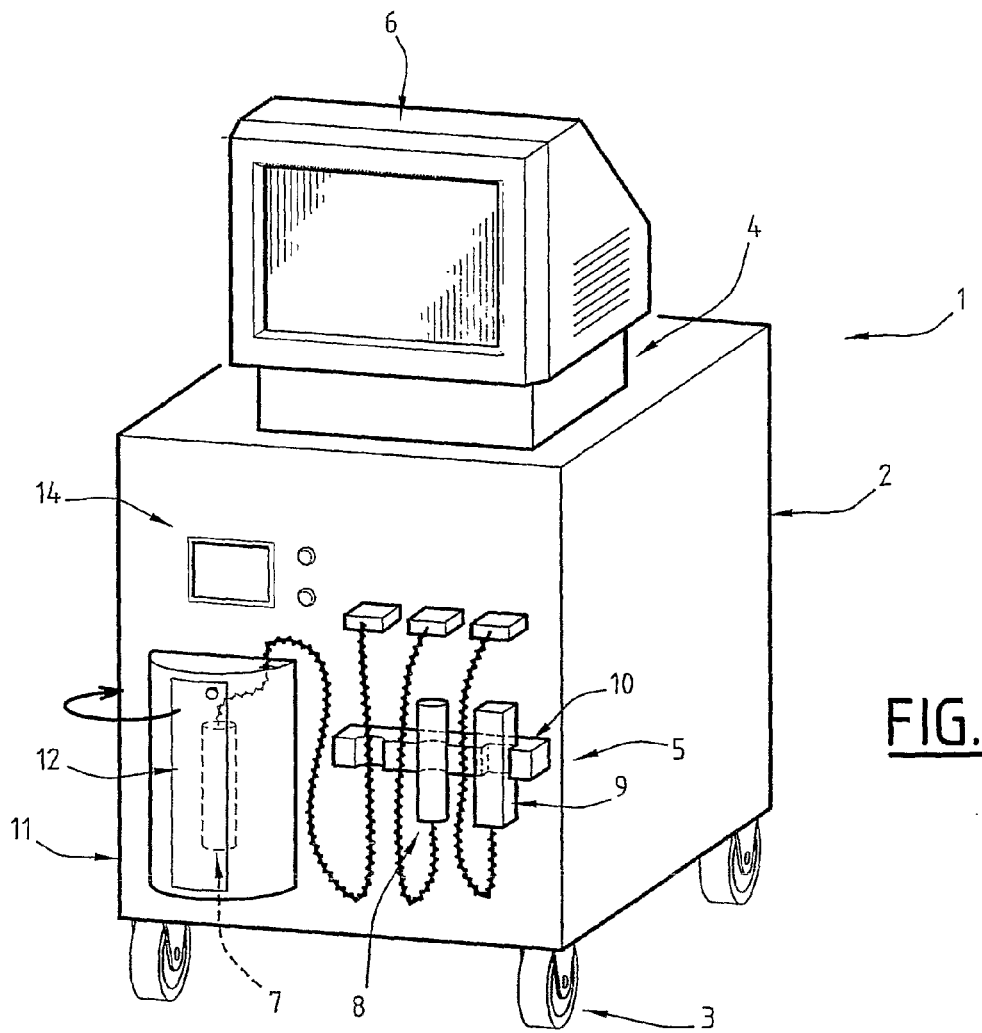
FIG. 1 is a perspective view of an example of embodiment of a medical imaging apparatus according to the invention.

In the example of embodiment illustrated on these Figures, this apparatus is constituted, for example, by a sonogram apparatus which is designated by the general reference numeral 1 on FIG. 1.

Thus, this apparatus comprises a frame designated by the general reference numeral 2, which is mounted, for example, on wheels, one of which is designated by the general reference 3, so as to be displaceable.

On this frame, various parts of the sonogram apparatus are mounted, such as, for example, a medical imaging data processing unit designated by the general reference numeral 4, connected at least to imaging sensor forming means designated by the general reference numeral 5 on this Figure, and means forming display monitor of these images designated by the general reference numeral 6.

Of course, it is understood that other parts and components can be provided, such as, for example, printing means, etc.

In the example of embodiment illustrated on this FIG. 1, the frame also comprises means for storing the sensors.

There are, for example, three sensors, designated by the general reference numerals 7, 8, and 9 on this Figure, and they actually comprise an active portion functioning as sensor connected by a connecting cable to a respective connector that makes it possible to connect the sensor to the rest of the apparatus, and in particular to the data processing unit of this apparatus.

The sensor storing means are, for example, designated by the general reference numeral 10 on this Figure, and they include any appropriate part for storing sensors, such as, for example, a member in the form of a comb for coupling to sensors, as illustrated.

Of course, it is understood that other embodiments can also be envisioned.

According to the invention, this medical imaging apparatus also comprises at least one integrated chamber for disinfection of the sensor forming means.

Such a chamber is designated, for example, by the general reference 11 on FIG. 1.

Figure 2:
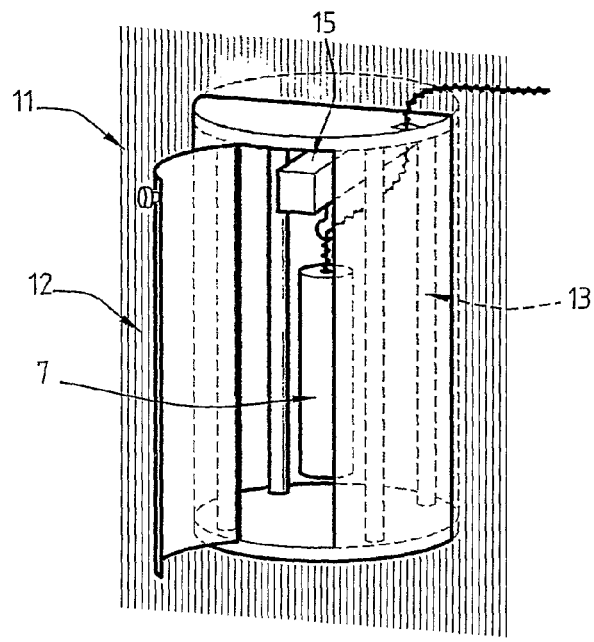
FIG. 2 is a detailed perspective view of an example of embodiment of a disinfecting chamber which is part of the constitution of an apparatus according to the invention.

Actually, as illustrated on FIGS. 1 and 2, such a chamber 11 is integrated into the frame of the apparatus and includes, for example, an access hatch designated by the general reference 12 on these Figures, which enables an operator to introduce a sensor, such as, for example, the sensor 7, into the chamber, in order to subject it to a disinfecting cycle.

A large number of embodiments of the access hatch can be envisioned. For example, this hatch can be articulated on the frame to enable an operator to open and close the chamber.

Then, the chamber 11 has means for generating a disinfection radiation for disinfection of the sensor, this radiation being, for example, a UV radiation, for example, a C type UV radiation.

In this case, the generation means comprise, for example, UVC tubes such as designated by the general reference numeral 13 on this FIG. 2.

A more detailed example of embodiment of these tubes and of their arrangement will be provided below.

Then, operation of this chamber is controlled by control means associated with, for example, a control panel designated by the general reference numeral 14 on this Figure, and provided on the frame 2 of the apparatus.

In addition, the chamber is also equipped with means for suspending the sensor in this chamber.

These suspension means are formed, for example, by a boom designated by the general reference numeral 15, enabling the operator to hang the cable 7 of the sensor, so as to maintain the sensor in suspended position in the chamber in order to optimize its disinfection.

The document EP-A-0 839 537 already describes a device of this type for supporting instruments in a chamber, in particular a decontamination chamber, and a corresponding chamber.

Then, it is understood that the integration of such a chamber into a medical imaging apparatus makes it possible to greatly facilitate the sensor disinfecting operations in-so-far the UV radiation disinfection is extremely effective and it is no longer necessary to disconnect/reconnect the sensor from the apparatus and to let it soak in a disinfection solution in order to obtain an effective disinfection.

That is, the passage of the sensor during a few minutes in the disinfection chamber makes it possible to obtain an optimal disinfection of this sensor, in a very simple manner for the operator, for example, between two patients.

Figure 3:
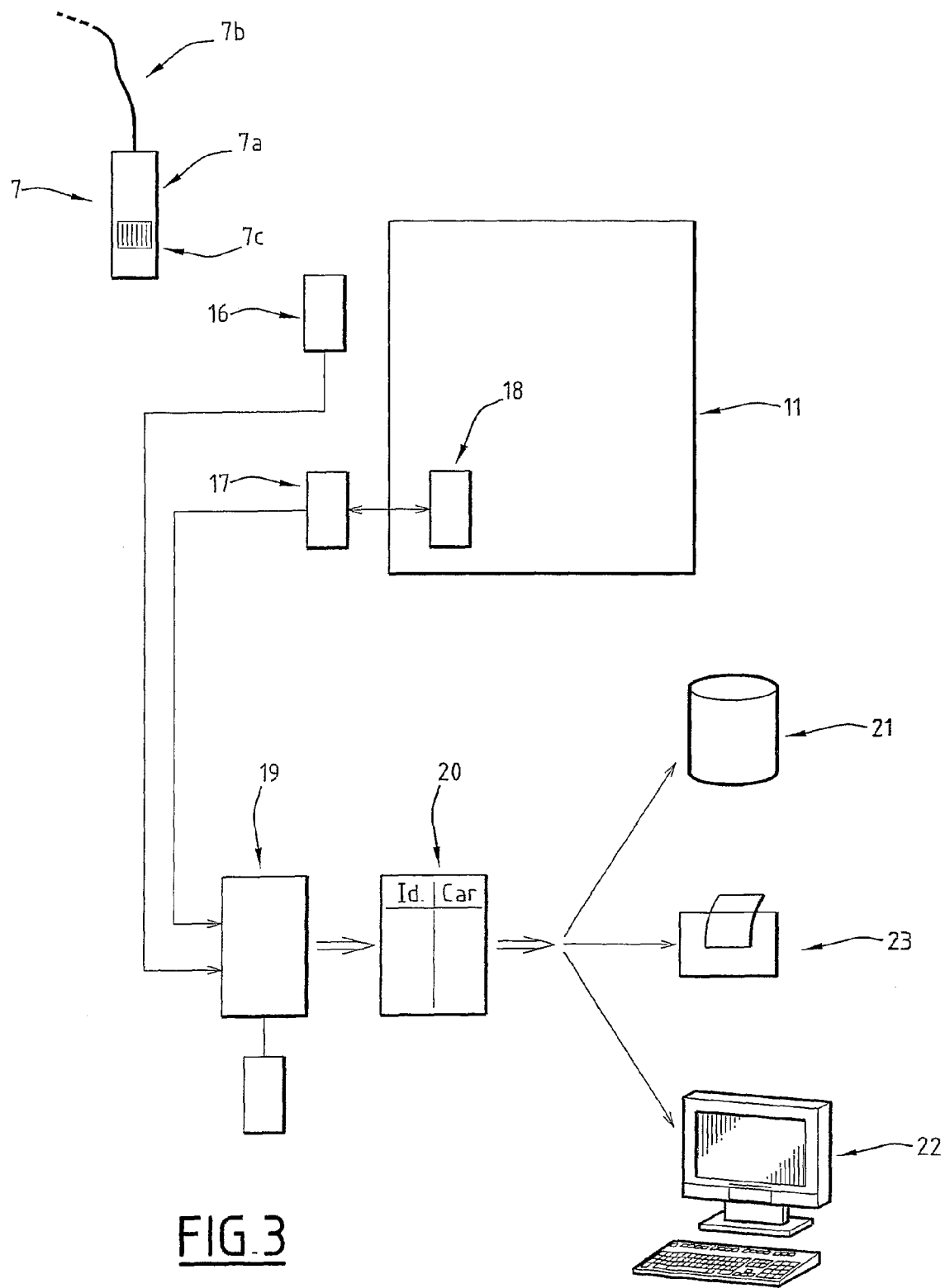
FIG. 3 is a schematic synoptic view illustrating the structure and operation of means for traceability of the disinfection of a sensor, which is part of the constitution of an apparatus according to the invention.

In addition, as illustrated on FIG. 3, means for traceability of the disinfection operation of the sensors can be envisioned.

Thus, FIG. 3 shows the disinfection chamber 11 and the sensor generally designated by the reference numeral 7.

Actually, as explained above, such a sensor generally comprises an active portion designated by the general reference numeral 7a on this Figure and a connecting cable designated by the general reference numeral 7b.

Thus, this sensor is adapted to be put in place and removed from the disinfection chamber 11, this disinfection chamber being adapted to implement a disinfecting cycle of this sensor, using disinfecting radiation.

In this regard, it will be noted that a cable opening is provided, for example, in the area of the access hatch or other, in order to make it possible to introduce the sensor into the chamber without disconnecting it from the rest of the apparatus.

In the apparatus according to the invention, each sensor carries identification data of this sensor.

By way of example, this identification data can be constituted by a bar code designated by the general reference numeral 7c on FIG. 3, this bar code being carried, for example, by the active portion, or by the connecting cable of the sensor.

Of course, other embodiments can be envisioned.

Then, the chamber is associated with means for acquiring this identification data of each sensor.

These means for acquiring this identification data are designated by the general reference numeral 16 on this FIG. 3, and comprise, for example, any appropriate sensing element, for example, a bar code reader or other.

This sensing element is then adapted to acquire the identification data of the or each sensor when it is put in place and when it is removed from the chamber at the start and at the end of a disinfecting cycle.

By way of example, these acquisition means can be in the form of a sensing element external to the chamber, for example, in the form of a "scanhead" type sensing element or in the form of a sensing element directly integrated into the disinfection chamber, for example, under the boom 15 of this chamber.

In addition, the chamber is associated with means for acquiring characterization data of the disinfecting cycle, i.e., more particularly, of the conditions of its performance.

These means are designated by the general reference numeral 17 on this Figure, and they can include various types of data acquisition means adapted to acquire data selected from a data group comprising, for example, identification data of the chamber and/or of the apparatus, each chamber/apparatus being then associated with a specific identification number stored therein, time-stamping data of the cycle, making it possible, for example, to acquire the date of the cycle, the number of the cycle in the day, the time at the start and the time at the end of the cycle, from a clock-forming circuit, etc.

This characterization data can also include data regarding the UV dose emitted during a cycle if the chamber is a disinfection chamber equipped with means for generating disinfecting UV radiation.

Then, this data can be determined from a sensing element of any appropriate type already known in the art and designated, for example, by the general reference numeral 18 on this Figure.

This sensing element can be implanted, for example, under the boom 15 of the chamber.

These various data, i.e., the identification data of the or each sensor and the characterization data of the disinfecting cycle, are then transmitted to a data processing unit designated by the general reference numeral 19 on this Figure and constituted by any appropriate computer, for example, integrated into the means for controlling the operation of the chamber, so as to implement a function of associating this data in order to generate traceability data of the disinfection.

That is, this data processing unit 19 is adapted to associate the identification data of the or each sensor present in the chamber during a disinfecting cycle with the characterization data of the performance of this cycle, in order to supply data making it possible to ensure the traceability of the disinfection of the or each sensor.

This traceability data is designated by the general reference numeral 20 on this Figure and makes it possible to relate each sensor to the conditions of the performance of the corresponding disinfecting cycle.

It is to be noted that this traceability data can be emitted only if a sensor has been identified when it is introduced into the chamber before the start of the cycle and when it is removed from this chamber after the end of the cycle.

Thus, the operator must necessarily identify the sensor when it is put in place and when it is removed from the chamber. If this is not the case, the data processing unit does not generate traceability data.

This traceability data is then available to ensure the traceability of the disinfection operation, in order, for example, to store this data in data storage means as illustrated at 21 on this Figure, to display this data, for example, on a display device of any type designated by the general reference numeral 22, or to print this data, for example, with printing means of any type such as a printer designated by the general reference numeral 23.

It will be noted that such a printer can, for example, be adapted to print the traceability data on a sticker that can be associated with, for example, a file of a patient that was in contact with the disinfected sensor, a traceability register, etc.

By way of example, then, the characterization data carried by this sticker includes data on a UV dose received by the sensor during its passage in the disinfection chamber, where this dose can be determined from the power or UV illumination emitted during the cycle multiplied by the duration of this cycle.

Indeed, it is known that this parameter can be crucial to obtain a specific level of disinfection of the sensors.

It is understood, then, that such a system makes it possible to ensure an optimal traceability of disinfection of sensors of this type in-so-far the traceability data makes it possible to guarantee the passage of the sensor in the chamber and to verify the characterization data of the disinfecting cycle to which the sensor was subjected, i.e., in particular, the moment when this disinfection took place, the chamber in which this disinfecting cycle was performed, and the dose, in particular UV dose, received by the sensor.

Of course, other embodiments can be envisioned.

Figure 4:
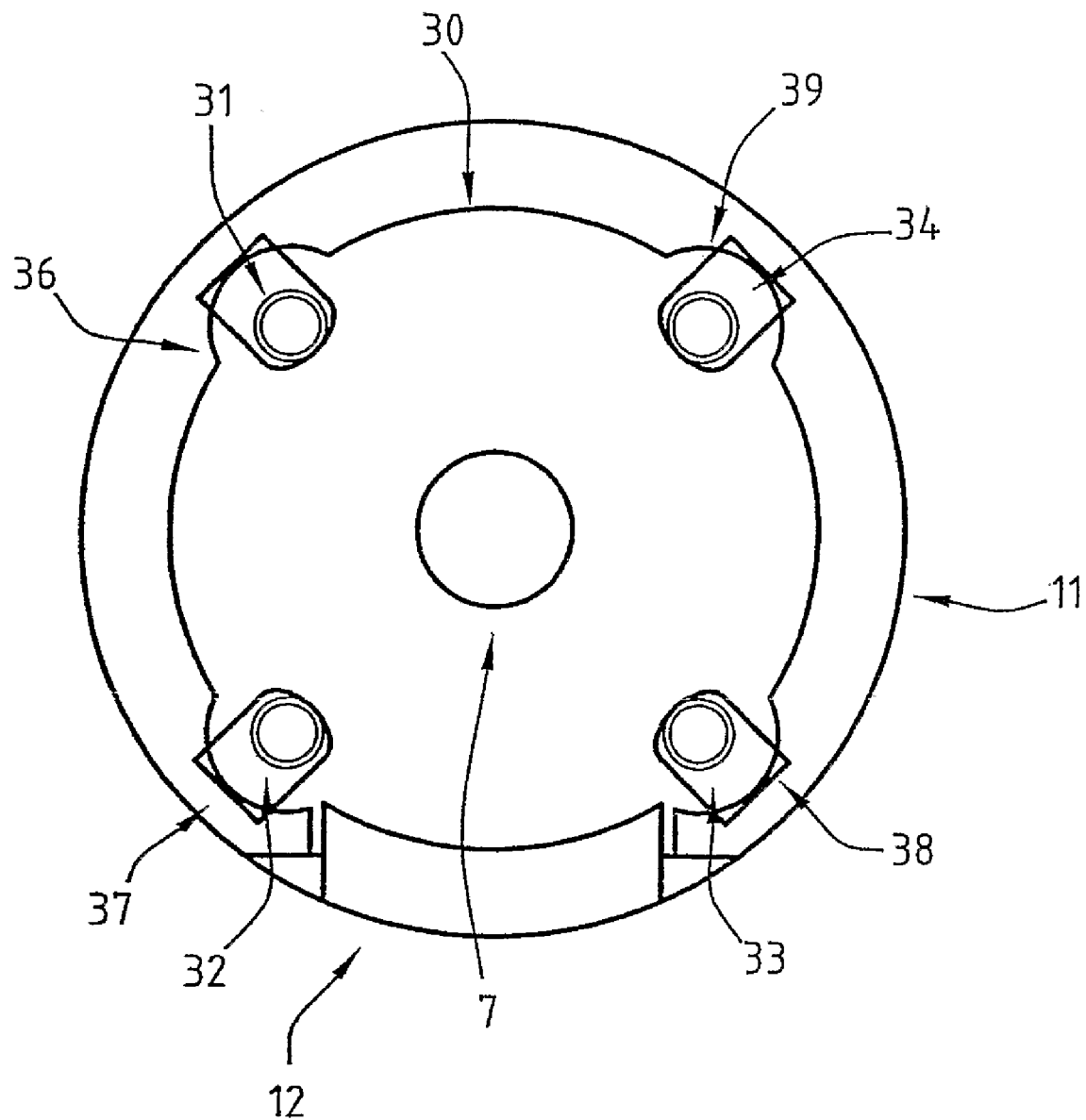
FIG. 4 is a cross-sectional top view of a portion of the chamber which is part of the constitution of an apparatus of the invention.

FIG. 4 illustrates an example of embodiment of such a disinfection chamber.

This disinfection chamber is also designated by the general reference numeral 11 on this FIG. 4, and the access hatch to this chamber is designated by the general reference numeral 12.

The sensor is still designated by the general reference numeral 7.

As illustrated, the chamber then has an inner surface having a circular cross-section, for example.

This surface is designated by the general reference numeral 30 on this Figure, and it makes it possible, then, to optimize the reflection of the radiation generated by the radiation generation means on the sensor to be disinfected.

In the example of embodiment illustrated on this FIG. 4, these generation means actually comprise four tubes designated by the general reference numerals 31, 32, 33, and 34, respectively, distributed, for example, at an angle of 90° with respect to one another in corresponding receiving semi-circular recesses provided in this inner surface of the chamber.

These semi-circular recesses are designated by the reference numerals 36, 37, 38, and 39, respectively, on this Figure.

Of course, it is understood that a different number of tubes and another arrangement of these tubes could also be envisioned.

In addition, the chamber can also be optimized, for example, if the inner surface 30 is covered at least in part and preferably completely by polytetrafluoroethylene (PTFE), also known under the trademark TEFLON. That is, it has been observed that the use of such a cover material on this surface makes it possible to also further optimize the reflection of the radiation and thus the quality of disinfection.

Thus, it is understood that such a structure and in particular the use of such an inner surface for the chamber make it possible to optimize the reflection of the radiation emitted by the means for generating such radiation in order to optimize disinfection of the sensor.

Figure 5:
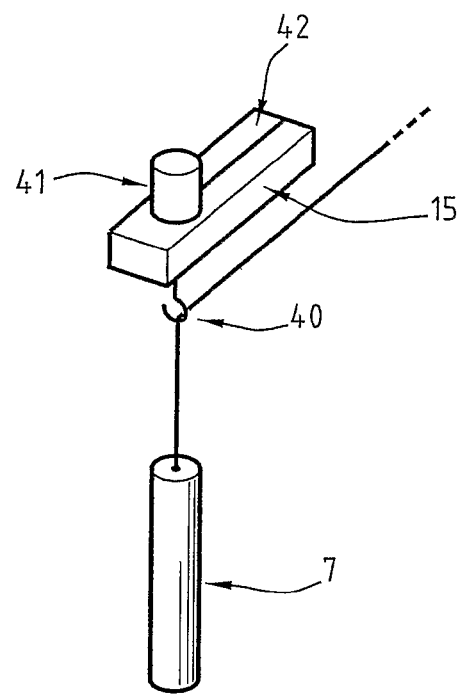
FIGS. 5 and 6 are detailed views of embodiments of this chamber.

FIG. 5 illustrates an improvement of such a chamber in which the boom 15 for suspending the sensor 7 includes means for rotating the sensor in the chamber.

Actually, this boom 15 participates to the constitution of means for suspending at least one sensor to be disinfected, in the chamber.

Advantageously, these suspension means can be, for example, adjustable in height in the chamber by any known adjustment mechanism, such as, for example, a screw-nut mechanism that the operator can maneuver using a knob.

Of course, other embodiments can be envisioned.

To remedy problems related to homogeneity of disinfection within the chamber, the means for suspending the sensor comprise means for rotating this sensor in the chamber, during its disinfection.

By way of example, a complete rotation about themselves or an oscillating movement over a predetermined angular range of these suspension means, and thus, of the sensor, can be envisioned.

In the example of embodiment illustrate don FIG. 5, these suspension means actually comprise a member in the form of a hook designated by the general reference numeral 40 to which the sensor designated by the general reference numeral 7 can be suspended, this hook being, for example mounted movable in rotation with respect to the boom 15 under the action of drive means designated by the general reference numeral 41 and including, for example, an electric motor associated with speed reduction means or other, whose output shaft is associated with the hook 40 in any appropriate manner.

This motor can be placed, for example, on the boom 15 perpendicularly to the hook.

Electrical supply to the motor is then provided by electrical conductors designated by the general reference numeral 42 on this Figure, which make it possible to connect these drive means to a unit for controlling the operation of the chamber, implanted in the apparatus, for example.

When the chamber is in operation, the drive means are then controlled so as to move the suspension means and thus the sensor, in order to homogenize the exposition of this sensor to disinfecting UV radiation, for example.

Of course, it is understood that other embodiments can be envisioned, in particular, regarding these suspension means and drive means.

Figure 6:
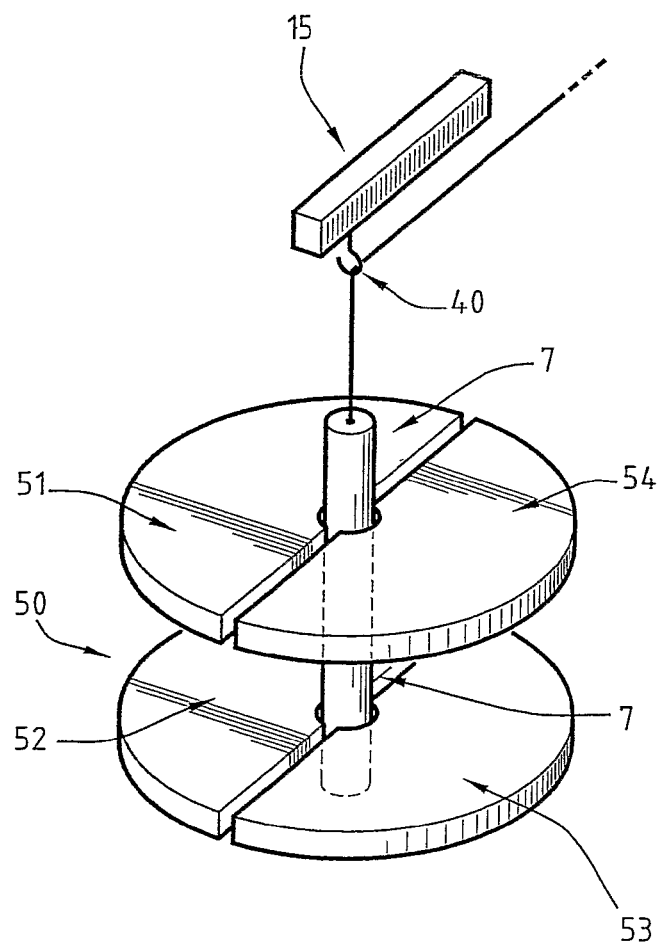

FIG. 6 illustrates still another improvement of this chamber.

As indicated above, such a chamber includes the boom designated by the general reference numeral 15, which extends in the chamber to participate in the constitution of the means for suspending the sensor to be disinfected in the chamber.

To further improve the quality of disinfection in the chamber according to the invention, means transparent to radiation are provided for holding the sensor in an elongated state and in a substantially vertical orientation, under the suspension means.

This makes it possible, for example, to avoid any deformation or twisting of the sensor, which could translate into a disposition and/or a state of this sensor that may be unfavorable to disinfection.

Various embodiments of these means for holding the instrument can be envisioned.

Actually, these holding means are adapted to hold the sensor preferably substantially at the center of the chamber, as illustrated.

These holding means can then include, for example, means for guiding the sensor such as those illustrated on this Figure and designated by the general reference numeral 50.

Indeed, in the example of embodiment illustrated on FIG. 6, these holding means comprise one or several members in the form of guiding combs distributed over the height of the chamber, to hold the instrument in an optimal disinfection position.

In the example illustrated, two series of two complementary combs designated by the reference numerals 51, 52, 53, and 54, respectively, are used at two different heights in the chamber to hold the sensor in the optimal position.

Of course, it is understood that other embodiments of these means can be envisioned. Thus, by way of example, one or several tubes for receiving one or several sensors can also be envisioned, these tubes extending, for example, in the area of the center of the chamber in a vertical position.

However, according to still another embodiment, these holding means can also be formed by a weight adapted to be coupled and/or suspended at the corresponding free end of the sensor in order to hold it in position.

Of course, as indicated above, these holding means are made in a material transparent to radiation, such as, for example, a C type UV radiation.

In this case, the holding means are made, by way of example, in silicium oxide.

Of course, it is understood that other embodiments can also be envisioned.

Then, holding the sensor in position makes it possible to ensure that it is in the most favorable position for its disinfection in the chamber.

It is then understood that such an apparatus has a number of advantages as compared to apparatuses in the state of the art, in particular regarding disinfection of the sensors.

That is, this disinfection can be implemented very easily and very quickly by an operator, in order to obtain an optimal disinfection of the sensors.

Of course, it is understood that various other embodiments of such an apparatus can be envisioned.

The invention claimed is:

1. Medical imaging apparatus, of the type including a frame on which is mounted at least one medical imaging data processing unit connected at least to imaging sensor forming means and to image display forming means, wherein the frame includes at least one integrated chamber for disinfecting the sensor forming means, including means for generating a disinfecting radiation and adapted to implement a disinfecting cycle thereof,
wherein each sensor has identification data and in that the chamber is associated with means for acquiring the identification data of the or each sensor when it is put in place and when it is removed from the chamber at the start and at the end of a disinfecting cycle, with means for acquiring characterization data of the disinfecting cycle, and with means for associating the identification data of the or each instrument and the characterization data of the disinfecting cycle to generate traceability data of the disinfection of the or each sensor.

2. Apparatus according to claim 1, wherein the chamber is equipped with an access hatch and is associated with a control panel provided on the frame.

3. Apparatus according to claim 1, wherein the identification data of each sensor is in the form of a bar code and in that the corresponding acquisition means of the chamber comprise a code reader.

4. Apparatus according to claim 3, wherein the chamber includes a boom for suspending the sensor and in that the reader is fixed to this boom.

5. Apparatus according to claim 1, wherein the means for acquiring characterization data of the disinfecting cycle comprise means for acquiring data selected from the data group comprising identification data of the chamber and/or of the apparatus and time-stamping data of the disinfecting cycle.

6. Apparatus according to claim 1, wherein the chamber includes means for generating a UV radiation for disinfecting the sensor and in that the characterization data of the disinfecting cycle comprises data on the UV dose emitted during the cycle, provided by a corresponding sensing element implanted in the chamber.

7. Apparatus according to claim 6, wherein the chamber includes a boom for suspending the sensor and in that the reader is fixed to this boom, and wherein the UV sensing element is implanted under the boom of the chamber.

8. Apparatus according to claim 1, wherein the means for associating the data are associated with means for displaying this data, for storing this data, and/or for printing this data.

9. Apparatus according to claim 1, wherein the means for associating this data are adapted to emit traceability data only if the corresponding sensor has actually been identified when it is put in place and when it is removed from the chamber before and after the disinfecting cycle, respectively.

10. Apparatus according to claim 1, wherein the chamber has an interior surface having a circular cross-section.

11. Apparatus according to claim 10, wherein the inner surface of the chamber has semi-circular recesses for receiving radiation generating means.

12. Apparatus according to claim 11, wherein the radiation generating means include four tubes disposed at 90° with respect to one another.

13. Apparatus according to claim 1, wherein the chamber has an inner surface covered at least in part by polytetrafluoroethylene (PTFE).

14. Medical imaging apparatus, of the type including a frame on which is mounted at least one medical imaging data processing unit connected at least to imaging sensor forming means and to image display forming means, wherein the frame includes at least one integrated chamber for disinfecting the sensor forming means, including means for generating a disinfecting radiation and adapted to implement a disinfecting cycle thereof;
  wherein the chamber has means for suspending at least one sensor in the chamber and means for rotating the sensor in the chamber.

15. Apparatus according to claim 14, wherein the rotating means are adapted to cause an oscillating movement over a predetermined angular range of the suspension means.

16. Apparatus according to claim 14, wherein the rotating means comprise electric drive means associated with a hook for suspending the sensor in the chamber.

17. Apparatus according to claim 16, wherein the chamber includes a boom for suspending the sensor and in that the reader is fixed to this boom, and wherein the suspension means and the drive means are associated with the boom extending in the chamber.

18. Medical imaging apparatus, of the type including a frame on which is mounted at least one medical imaging data processing unit connected at least to imaging sensor forming means and to image display forming means, wherein the frame includes at least one integrated chamber for disinfecting the sensor forming means, including means for generating a disinfecting radiation and adapted to implement a disinfecting cycle thereof;
  wherein the chamber has means for suspending at least one sensor in the chamber and means for generating a disinfection radiation in the chamber, and means transparent to the radiation for holding the sensor in an elongated state and in a substantially vertical orientation under the suspension means.

19. Apparatus according to claim 18, wherein the holding means are adapted to hold the sensor substantially at the center of the chamber.

20. Apparatus according to claim 18, wherein the holding means comprise means for guiding the sensor in the chamber.

21. Apparatus according to claim 20, wherein the guiding means include one or several members in the form of combs for guiding the sensor distributed over the height of the chamber.

22. Apparatus according to claim 21, wherein the guiding means comprise one or several tubes for receiving the sensor.

23. Apparatus according to claim 18, wherein the holding means comprise a weight adapted to be coupled to the free end of the sensor.

24. Apparatus according to claim 18, wherein the holding means are made in silicium oxide.

25. Apparatus according to claim 18, wherein the holding means are located under the suspension means.

* * * * *